United States Patent
Mueller et al.

(10) Patent No.: US 6,981,289 B2
(45) Date of Patent: Jan. 3, 2006

(54) CHANGE AIDS FOR EXTERNAL ARTICLES

(75) Inventors: Joerg Mueller, Karben (DE); Mattias Schmidt, Idstein (DE); Lars Westerheide, Kelkheim (DE); Mark James Kline, Okeana, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/764,849

(22) Filed: Jan. 26, 2004

(65) Prior Publication Data

US 2004/0158218 A1    Aug. 12, 2004

Related U.S. Application Data

(63) Continuation of application No. PCT/US02/23644, filed on Jul. 25, 2002.

(30) Foreign Application Priority Data

Jul. 26, 2001    (EP) .................................. 01117671

(51) Int. Cl.
A47C 20/02      (2006.01)
B68G 5/00       (2006.01)
A47B 13/00      (2006.01)
A47B 7/02       (2006.01)
A47B 17/06      (2006.01)

(52) U.S. Cl. .............................. 5/655; 5/603; 206/440; 604/385.01

(58) Field of Classification Search ............ 604/385.01, 604/385.02, 385.06; 206/438, 440, 824; 5/603, 655; 4/551, 572.1; 128/869
See application file for complete search history.

(56) References Cited

U.S. PATENT DOCUMENTS

| 3,367,334 A |   | 2/1968  | Testa |
|-------------|---|---------|-------|
| 3,462,773 A | * | 8/1969  | Triplett .......................... 5/111 |
| 3,489,194 A | * | 1/1970  | Hoover .......................... 383/4 |
| 3,973,567 A |   | 8/1976  | Srinivasan et al. |
| 4,781,277 A | * | 11/1988 | Lim ............................. 190/1 |
| 4,862,535 A | * | 9/1989  | Roberts ......................... 5/655 |
| 4,964,859 A |   | 10/1990 | Feldman |
| 4,989,286 A | * | 2/1991  | Tucker .......................... 5/482 |
| 4,999,863 A | * | 3/1991  | Kane ............................. 5/98.1 |
| 5,125,121 A | * | 6/1992  | Wroble ......................... 5/484 |
| 5,208,925 A | * | 5/1993  | Edlund ......................... 5/424 |
| 5,233,714 A | * | 8/1993  | De Bell Daniel .............. 5/655 |
| 5,299,336 A | * | 4/1994  | Marteeny ....................... 5/655 |
| 5,304,158 A | * | 4/1994  | Webb .................... 604/385.13 |
| 5,439,008 A | * | 8/1995  | Bowman .................... 128/875 |

(Continued)

FOREIGN PATENT DOCUMENTS

GB        2298627 A      9/1996

*Primary Examiner*—Larry I. Schwartz
*Assistant Examiner*—Michael G. Bogart
(74) *Attorney, Agent, or Firm*—Michael P. Hayden; Matthew P. Fitzpatrick; Ken K. Patel

(57) ABSTRACT

An external change aid having engaging means which can engage with a landing member on an absorbent article and having a specific peel force and/or shear force when engaged with such an absorbent article. Also provided are combinations of such external change aids and absorbent articles and methods for applying an absorbent article by use of the external change aid. Also provided are external change aids having specifically designed engaging means structures and absorbent articles with specifically designed engaging means structures.

20 Claims, 7 Drawing Sheets

U.S. PATENT DOCUMENTS

| | | | |
|---|---|---|---|
| 5,615,433 A * | 4/1997 | Martin | 5/655 |
| 5,706,950 A | 1/1998 | Houghton et al. | |
| 5,746,219 A * | 5/1998 | McConnell | 128/845 |
| 5,987,677 A * | 11/1999 | Betker | 5/655 |
| 6,036,679 A | 3/2000 | Balzar et al. | |
| 6,055,688 A * | 5/2000 | Helmsderfer et al. | 5/655 |
| 6,293,932 B1 * | 9/2001 | Balzar et al. | 604/385.02 |
| 6,298,993 B1 * | 10/2001 | Kalozdi | 206/581 |
| 6,405,394 B1 * | 6/2002 | Rosenberg | 5/655 |
| D467,117 S * | 12/2002 | Guy | D6/596 |
| 6,694,552 B1 * | 2/2004 | Vickers | 5/655 |
| 6,708,356 B1 * | 3/2004 | LaValle | 5/655 |
| 2001/0056270 A1 * | 12/2001 | Mizutani et al. | 604/385.02 |
| 2004/0211003 A1 * | 10/2004 | Stackman et al. | 5/655 |

* cited by examiner

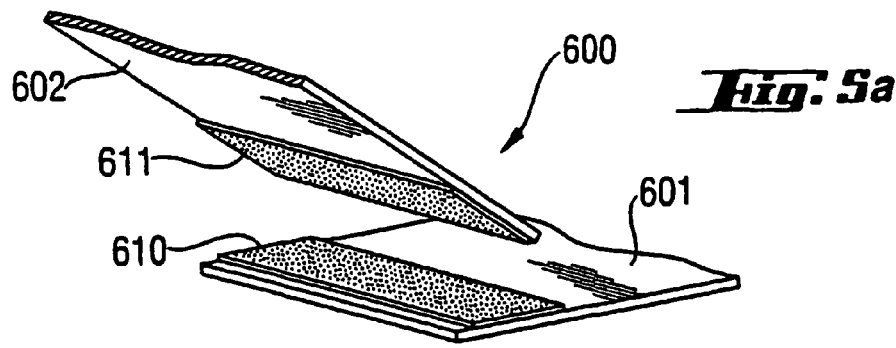
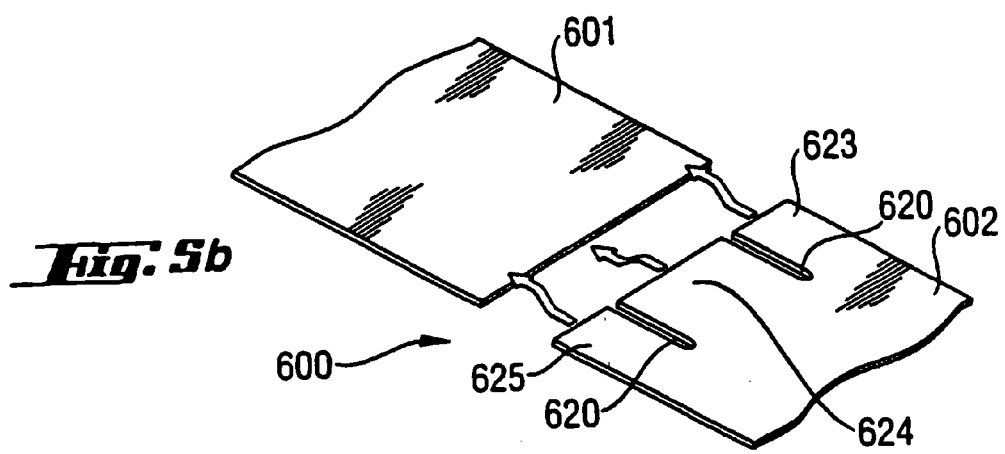
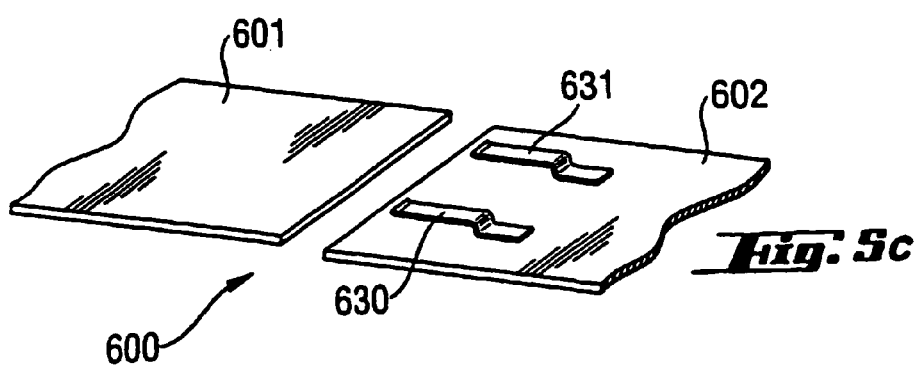
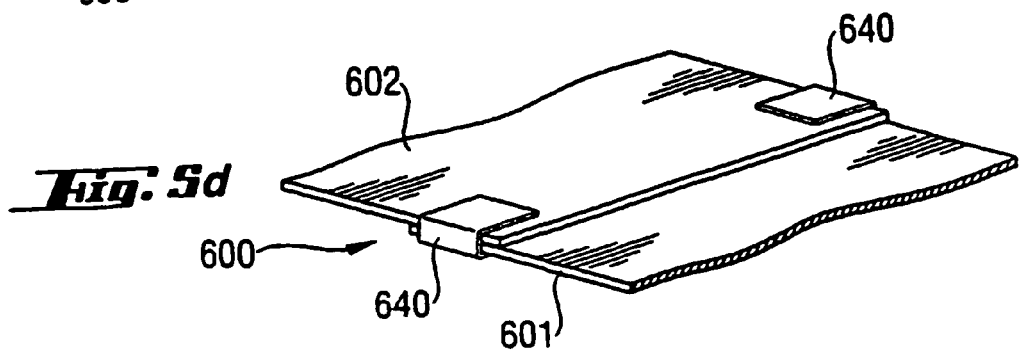

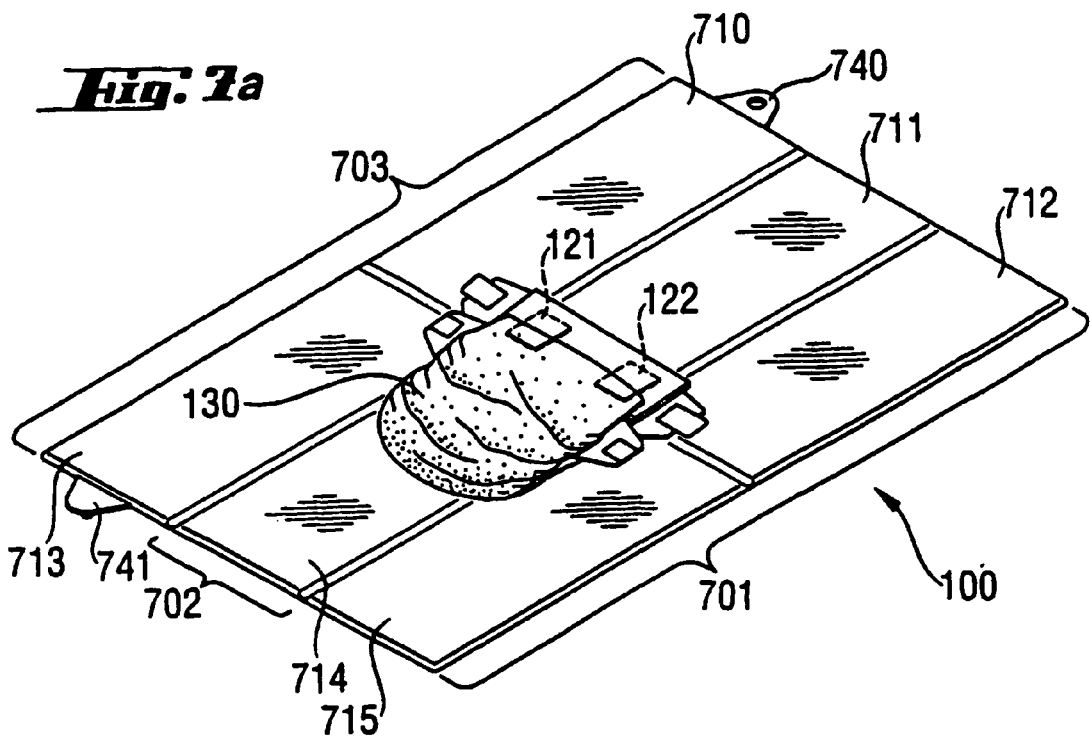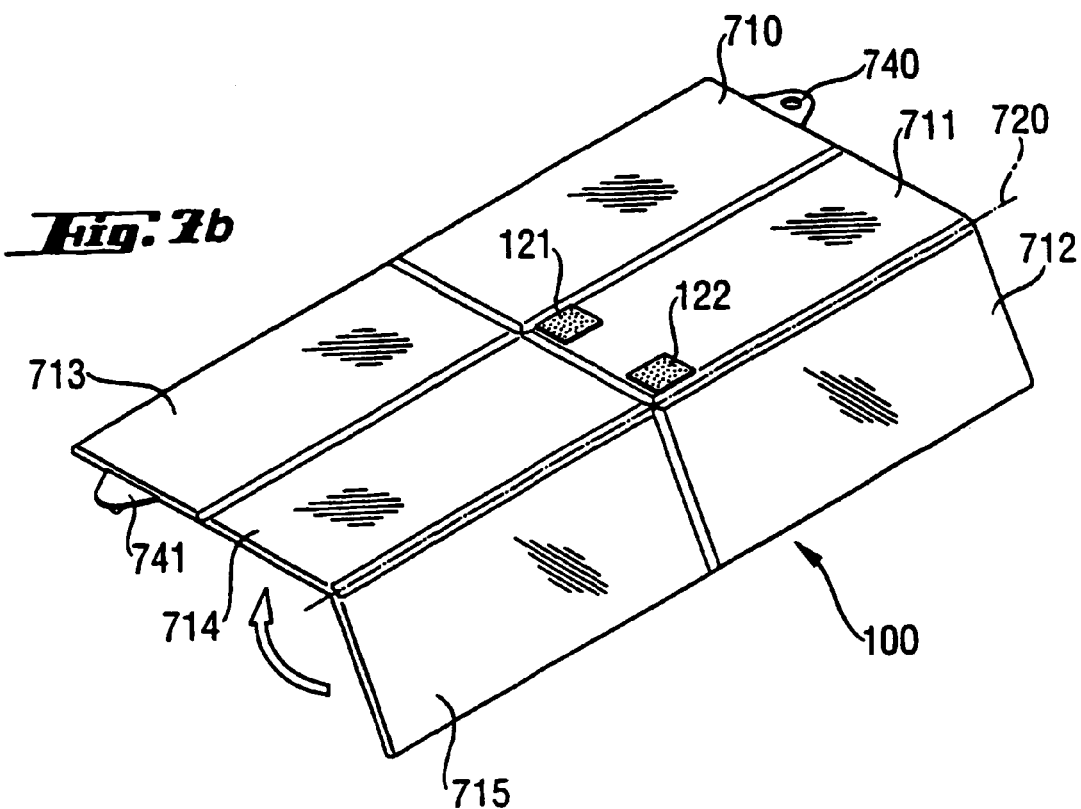

CHANGE AIDS FOR EXTERNAL ARTICLES

CROSS-REFERENCE TO RELATED APPLICATIONS

This application is a continuation of co-pending International Application No. PCT/US02/23644 filed on 25 Jul. 2002 and published as International Publication No. WO 03/009727 A1 on 6 Feb. 2003, which claims priority to European Application EP 0 111 767 filed on 26 Jul. 2001.

FIELD OF THE INVENTION

This invention is directed to devices that assist in the application or removal of articles worn primarily externally on the body of the wearer, especially hygienic absorbent articles, such as diapers, adult incontinence articles, feminine protection articles and the like. The invention also relates to a combination of such devices and such articles, which can engage with one another, and to specially designed articles. The invention also relates to methods of application or removal of articles using the devices of the invention.

BACKGROUND OF THE INVENTION

Articles worn externally to the body of the wearer, such as diapers, are commonly misapplied due to awkward positioning of the wearer for application or the restless movement of the wearer. This problem is even more apparent when the article, such as a diaper, does not easily stay in the position required for application, for example if the article has a tendency to fold, roll-up etc. This can be particularly the case if the article has elastic components, such as elastic leg cuffs or an elastic topsheet. Such articles have to be flattened or straightened prior to application and the elastic forces can make this difficult. The elastic forces can also cause the articles to fold back or roll back into the original position, if not enough force remains applied onto the article during application or removal, for example, if the caregiver or user lets go of one straightened end of the article, before the article is properly applied, or if the body of the wearer moves to much, and thereby removes the force which keeps the article straightened.

This can not only make the application of such articles troublesome, but it may also result in an uneven fit, gaps which result in leakage, and misplaced parts (such as fasteners) which may result in marking the skin of the wearer, and/or discomfort. Further, even if caregivers or wearers properly apply the product, they often speak of needing an extra hand to make the change process easier. This is particularly true when folded articles or elastic articles are to be applied or removed, or when dealing with uncooperative wearers such as babies. Babies, even from a young age, move their legs into awkward positions, roll from side to side, or even violently resist diaper changes using hand and leg motions. As a result, the caregiver often has to hold portions of the wearer's body as well as the diaper during the change process.

Certain prior art documents have attempted to improve the diaper change process by securing the wearer with restraints. However, restraints have been found to cause discomfort to the wearer, causing them to further resist, which makes the changing process more difficult. The prior art attempts have so far failed to adequately facilitate a convenient and comfortable means of changing articles worn external to the body, and thus, problems still exist relating to ease of application and removal of articles worn primarily on the external surface of the body of the wearer.

It would be desirable to have a device that assists the caregiver or wearer in the process of changing articles worn external to the body of the wearer, in particular folded or elasticated articles. It would also be desirable to provide externally worn articles that contain elements uniquely designed to work with such a device to improve the ease and effectiveness of the article changing process.

SUMMARY OF THE INVENTION

The present invention provides an external change aid (preferably mat) for assisting in the application or removal of absorbent articles worn externally on the body of a wearer, which has an engaging means, engageable with said article, said engaging means being capable to provide a shear force of at least 5 N.

The invention also provides preferred changing mats for assisting in the application or removal of absorbent articles worn externally on the body of a wearer, including a change mat, having a planar side which has a top portion and a bottom portion (closest to the person applying the article), whereby the bottom portion comprises an engaging means in the form of one or more engaging members in the form of stripes, rectangles, dots, circles or triangles, which comprise engaging elements selected from hooks, loops adhesives or cohesives.

BRIEF DESCRIPTION OF THE DRAWINGS

FIG. 1b shows a schematic planar top view of the change mat of FIG. 1a.

FIGS. 5a, 5b, 5c and 5d show perspective views of alternative change aids (portion thereof) with two parts and alternative means to make the parts of the change aid stiff or rigid, e.g. restrict the relative movement between the parts.

FIG. 6b shows a side view of a part of the change aid of FIG. 6a.

FIG. 7a shows a top view of a foldable change mat, in an unfolded state, having a diaper engaged to the engaging means on the change mat.

FIG. 7b shows a top view of the foldable change mat of FIG. 7a in a partially unfolded condition.

DETAILED DESCRIPTION OF THE INVENTION

Figure 1A:
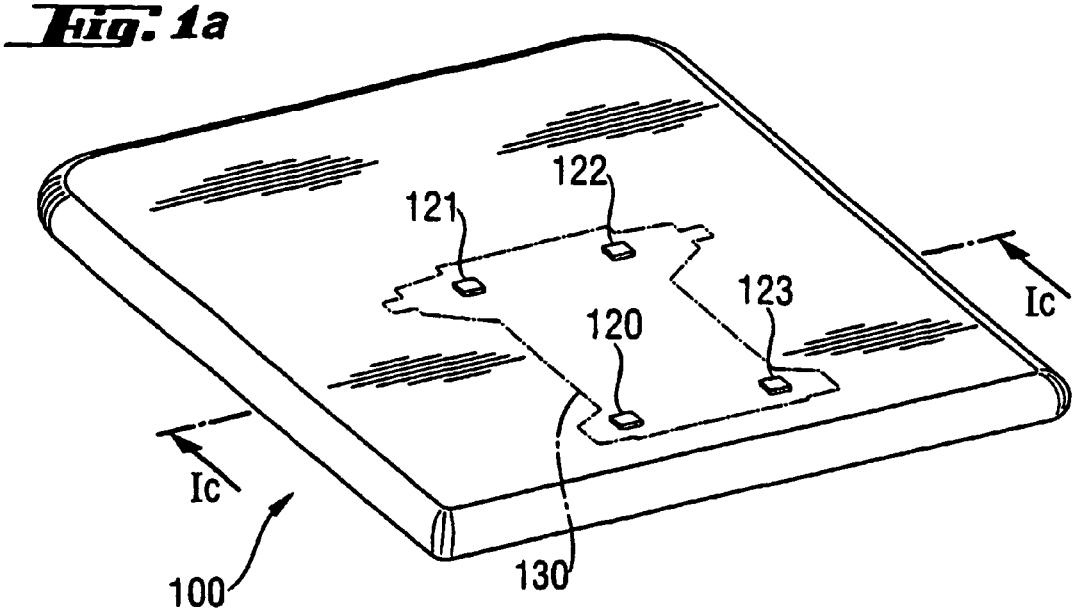
FIG. 1a shows a top view of a rigid change mat of the invention having four rectangular engaging members.

The present invention relates to external change aids which assist in the application or removal (i.e., changing) of articles worn external to the wearer's body including incontinence devices and absorbent articles such as colostomy bags, diapers, sanitary napkins, panty liners, bandages, body wraps, and the like. The article may be worn primarily external to the body of the wearer, but may include portions that are internal to the body.

The external change aid herein is a device which does not become or remain part of the article after application of the article; thus, the external change aid is a device which aids the initial application on the wearer or the final removal of the article, but which does not serve to keep the article in place on the wearer in use, once applied.

The external change aid comprises an engaging means. This engaging means is engageable with an article, typically with a landing member comprised by the article, such that the external change aid helps to apply or remove from the wearer; typically, the engaging means comprises one or more first engaging members which are engageable with second engaging members, comprised by a landing member of the article. The engaging means and landing member when used in combinations herein are referred to as an engaging system.

Thus, the engaging means and landing member, and the first and second engaging members thereof, are typically such that the external change aid and the article are removably, i.e. temporarily and releasably, fastened to one another, such that application to or removal of the article from the wearer is facilitated.

The landing member may for example be a member attached to the article to enable the engagement, such as an attached strip, rectangle or dot of engageable material such as VELCRO, or a multitude of such members, or the landing member may be an integral, functional part of the article, for example the backsheet of the article.

For example, the engaging means may be present over an entire surface (or even all surfaces) of the change aid, provided the change aid has the stiffness or rigidity as defined herein, and/or comprises restraining means as defined hereinafter. However, it may be preferred that the change aid has engaging means on only part of a surface or part of several surfaces, as described hereinafter in more detail.

In order to provide effective engagement of a broad range of articles, such as folded articles or articles having elastic components, the change aid is capable of providing a shear force of at least 5 N or even at least 7 N, preferably up to 16 N or more preferably up to 25 N or even preferably up to 30 N or even up to 35 N or even more preferably up to 45 N or even up to 55 N. This means for the purpose of the invention that the change aid has an engaging means which can provide a shear force of the values above, when engaged with an article (e.g. a landing member of an article), such that the formed engaging system has such a shear force. Of course it is to be understood that certain engaging means described herein engage with certain engaging means and that if the correct combination is formed, this shear force is provided. For example, if the engaging means has as engaging elements a number of hooks, the shear force of this hook-engaging means, when engaged with landing members suitable to form an engaging system such as loops, has to be for the purpose of the invention, at least 5 N, and then, the engaging means is for the purpose of the invention capable of providing this shear force. Hereinafter, it is described in more detail, which engaging means are suitably engaged with which landing members.

Thus, the combination of the change aid and the article of the invention, as described and claimed herein, has also a shear force of at least 5 N or even at least 7 N, preferably up to 16 N or more preferably up to 25 N or even preferably up to 30 N or even up to 35 N or even more preferably up to 45 N or even up to 55 N.

The engaging means of the change aid and therefore the engaging system, formed by the change aid, has typically a peel force of at least 2 N, or even at least 3 N. The change aid preferably has a peel force up to 10 N, or even up to 8 N or even up to 7 N. Most preferably, the change aid has a shear force between 5 N and 16 N and a peel force between 3 N and 5 N. This has for the purpose of the invention the same meaning as set out above with respect to the shear force.

The shear force and peel force can be obtained by use of the following method.

A Universal or Zwick tensile tester is prepared/calibrated to conform to ASTM D76. The load cell (conform ASTM E-4) is preferably chosen such that the results are between 10% and 90% of the capacity of the range. The gauge is set to a suitable length, e.g. 76 mm. The speed of the movement of the clamp is set to be 305 mm/min. The equipment is conditioned to 23° C. and 50% relative humidity and the whole test is also performed under these conditions.

The equipment has two clamps with centers in the same plane, parallel to the direction of the motion of the clamp, and so aligned that they will hold the change aid/article wholly in the same plane. The faces of the clamps are at least as wide as the leaders to be held by the clamps.

The change aid and article to be tested are conditioned at 23° C. and 50% relative humidity for 2 hours.

The change aid and article are connected in the manner done in normal use and it is determined which area of the change aid and article are connected, herein referred to as the area of the engaging means and the area of the landing members. This could thus for example be about the whole area of the change aid and a part of the article, but for example in a preferred embodiment, this would be only a strip of the change aid and a strip of about the same size of the article.

The areas of the engaging means and of the landing member, as determined above, are removed from both the change aid and the article, respectively. Each is separately adhered to a paper leader using double-sided tape. The leader is attached to the engaging means in a manner comparable to the manner in which the engaging means was attached to the changing aid or article (i.e., if an edge of the engaging means was loose when the engaging means was attached to the article, the same edge and same amount of the edge should be loose when attached to the leader).

Typical copier paper provides a suitable leader for most testing, but other suitable (thicker/heavier) paper can be easily chosen if more suitable. The leader should be the same width as the engaging means and cover the full length of the engaging means and extend at least 50 mm beyond the edge of the engaging means.

The direction the leader extends depends on whether shear or peel testing is to be performed. For peel testing, peel starts from a first edge of the engaging means and landing member area and finishes at a second edge of the areas, thus the leader extends from the first edge of the engaging means and landing member area. For shear testing, the leader on the change aid engaging means area extends from the first edge of this area, while the leader on the article landing area extends from the second edge of this area.

The change aid engaging means area is again placed on top of the article engaging means area in the position it would have in use—that is, the relative orientation of the areas (i.e., first edge to first edge) are to be maintained. The two samples are then manually pressed together (finger-thumb), such that the whole area to be engaged is pressed for about 3 seconds.

The article landing member area and leader is placed in the clamp, which is to be moved. The change aid engaging means area leader is placed in the stationary clamp, at the opposite end of the first clamp. The areas should be centered between the initial positions of the clamps. For large samples, a gauge length larger than 76 mm may need to be selected. A gauge length should be chosen such that there is at least 25 mm of leader between the edge of the clamp and the edge of the sample.

Then, the tensile tester movement and force measurement are started.

For the shear testing, the leader with the landing member area is pulled by the clamp with a force in the plane of both the areas on the leaders. For shear testing, maximum or peak force to completely disengage the two areas on the leaders is recorded. This is typically not the force at the moment just before the system becomes completely disengaged, but this mostly occurs before then. This peak shear force is for the purpose of the invention thus at least 5 N.

For the peel force testing, the engaged areas, before the test starts, are in an approximately horizontally position. The upper leader with the area of the article, gripped in the upper clamp, moves out of plane in a direction upwards, which is as much as possible perpendicular to the original horizontal position, thereby applying a peel force on the leaders with the areas and disengaging the areas. The other leader with the area of the change aid moves also out of plane in a direction downward, which is as much as possible perpendicular to the original horizontal position.

Thus, the angle of each of the leaders compared to the original horizontal position is as close to 90° (upwards or downwards) as the stiffness, size or type of material of the area permits. This engaged and disengaged areas and leaders thus have as much as possible the usual T-shape during the disengagement, as normally used in peel force methods.

For peel testing, the 4 highest peak forces are recorded up to the moment that the engaged areas on the leaders system are completely disengaged. The average of these 4 highest peak forces is calculated and reported as the result. The average of 4 highest peak forces is for the purpose of the invention the peel force of preferred embodiments of the invention, as described hereinafter.

The above tests can be applied to any surface fastener. The peel test, however, may not be applicable to certain types of interlocking fasteners, such as many types of buckles because certain types of interlocking fasteners cannot be peeled apart (such as those disclosed in WO 99/11211). In such cases in which a fastener has no peel-mode failure, only shear is measured.

Typically, the external change aid is stiff or rigid. This is useful, because the stiffness of the change aid ensures that the change aid does not move or fold, or only partially moves or folds along with the article, when forces are applied to it by the article or the user, e.g. elastic forces of the elasticized article, forces occurring when disengaging the article.

When used herein, a stiff or rigid change aid means for the purpose of the invention that the aid has the following behavior:

When the change aid is placed on a flat, planar, horizontal surface and two opposite ends of the change aid, spaced apart by a length L (typically in the direction parallel to the longitudinal direction of the change aid), are pushed toward one another in this horizontal direction with a force of 4 N, or even with a force of 6 N or even 8 N or even 12 N, the ends move closer toward one another with a displacement (length) L* which is less than 20% of L. Thus for example, if two opposite ends are placed in two opposing holders, and the distance L between the opposing edges of the holders is 50 cm, and a total force of 4 N is applied in horizontal direction on the holders and thereby thus on the change aids, by applying 2 N force in horizontal, opposing directions on each end, then the ends should be pushed together with a displacement L* of less than 10 cm.

Preferred may be that the change aid is more stiff, namely that the displacement L* is less than 10% or even less than 5%, or even about 0%.

When used herein, "longitudinal" is generally a direction running parallel to the maximum linear dimension, typically the longitudinal axis, of the article and includes directions within 45° of the longitudinal direction. 'Length' of the article or component thereof, when used herein, generally refers to the size/distance of the maximum linear dimension, or typically to the size/distance of the longitudinal axis, of an article or part thereof.

The "lateral" or "transverse" direction is generally orthogonal to the longitudinal direction, e.g. in the same plan of the majority of the article and the longitudinal axis, and the transverse direction is parallel to the transverse axis. 'Width' of the article or of a component thereof, when used herein, refers to the size/distance of the dimension orthogonal to the longitudinal direction of the article or component thereof, e.g. orthogonal to the length of the article or component thereof, and typically it refers to the distance/size of the dimension parallel of the transverse axis of the article or component.

'Thickness' of the article or component thereof, when used herein, refers to the size/distance of the dimension orthogonal to both the longitudinal and transverse directions, e.g. running parallel to the minimum linear dimension of the article.

The engaging means and landing member each typically comprises one or more engaging members, respectively first and second engaging members. The first engaging members of the engaging means can be any elements capable of engaging with second engaging members (of the landing member), to thus engage items together, such as the external change aid and the article. Said first and second engaging members are often also referred to as male and female engaging means or fastening means.

Thus, the first and second engaging members may be identical, provided that they are capable of engaging with one another. Such engaging members are often referred to as hermaphroditic engaging or fastening elements. More typically though, the first engaging member is different from the second engaging member, and each is selected such that the required engagement and engaging system is obtained. Preferred examples are described hereinafter.

The engaging means typically has one or more first engaging members, which each comprise said first engaging elements, and the landing member typically has one or more second engaging members comprising second engaging elements.

In a preferred embodiment the means comprises a plurality of first engaging members, which each comprising the first engaging elements. In a preferred embodiment herein the engaging members are separated from one another, so that there are areas without engaging elements in between engaging members. For example, the engaging means can be a plurality of engaging members which are in the form of lines or dots (with therein in between areas no comprising engaging elements); thus, the external change aid may have said engaging means in the form of a plurality of lines or dots, divided over one or more of its surfaces.

Equally, the landing member may comprise a plurality of second engaging members, which each comprising the second engaging elements, in an equal manner as described above.

The change aid is most useful for the application of articles, which have one or more elastic components, such as elastic leg cuffs, or more importantly an elasticized topsheet. Thus, in a preferred embodiment, the change aid is used for the application or removal of articles with elastic properties, typically those having specific elastic profiles as described hereinafter. The change aid is in particularly useful for the application of diapers.

In one aspect of the invention, the change aid is in particular useful to apply or remove articles, such as diapers, which require a high force to be straightened or flattened. In particular, the change aid is useful to apply or remove articles which require a shear force, as defined above, typically of at least 5 N, or even at least 7 N, or even at least 8 N, or even more than 12 N or even more than 16 N, and typically up to 55 N or even up to 45 N, to flatten them out to at least 80% of their full length. In another aspect the change aid is in particularly useful to apply or remove articles, which after flattening, tend to re-assume their lower energy or non-flattened state again, e.g. a stretched elastic article may snap back to unstretched position. Such articles typically require a shear force of at least 1 or even at least 2 N or even at least 3 N or even at least 5 N to be stretched or flattened to a length of 50% or even 70% or even 80% of their full length.

Preferred may be that the change aid has also restraining means. When used herein, the restraining means is any means capable to restrict the relative movement of the change aid. This includes restriction of the change aid relative to an external object, other than the wearer or the article (for example thus relative to a changing table, commonly used to change diapers on baby's), but also restriction of the movement of at least one part of the change aid, relative to at least one other part of the change aid.

Typically, this can be achieved by providing the change aid with restraining means which have surface fastening elements or interlocking elements, and/or restraining means which fasten two or more parts of the change aid such that they relative movement of the parts, relative to one another, is limited. Preferred examples are described hereinafter.

The restraining means is not to be engaged with the first or second engaging means, or in other words, the restraining means when present on the change aid herein does not form part of the engaging system. Thus, whilst an external change aid may comprise a restraining means with restraining elements which are equal or similar to the engaging members on that change aid, it is to be understood that the restraining means is then positioned on the change aid in such a position, shape or orientation that the intended use thereof is not to become part of the engaging system, or in other words, that the restraining elements of the change aid can not engage with the landing member or the second engaging members of the article, once the restraining elements function to restrict the relative movement. For example, the restraining means can be present on an opposite side of the change aid compared to the engaging means, so that when the restraining means are in use and restrict the movement of the change aid, they can not engage with the second engaging members of the article when brought into contact with the change aid, because the side of the restraining means faces away from the article. For example, the change aid may be a planar change mat, having a first planar surface with first engaging means on a first side and a second planar surface with restraining means on an opposite side, and then the mat can be placed with the side with the restraining means (flat) on an external object, so that the restraining means face the external object, which can then be connected to said object to restrict movement of the change aid; then, the surface facing upwards, away from the object, does not comprise any restraining means but only engaging means, which can then be engaged to (the landing member) of an article, placed on top of said change mat.

The following is a description of the preferred embodiments of the invention herein.

Engaging Means, Structures and Elements

The engaging means and landing member each comprise engaging members, respectively first and second engaging members. Since the change aid is to be engaged with the article, the first and second members are selected such that they can engage with one another and such that they form an engaging system as defined herein. This is often referred to as male and female engaging members. For the purpose of the invention, the change aid may comprise a male or female engaging members (or even both); thus, for example, if the combination of the first and second engaging members is a combination of hook fasteners and loop fasteners, the change aid may comprise either or both of these types of engaging members, and equally, the article may comprise either or both, provided that the engaging means and landing member are selected such that an engaging system is formed. The engaging means may also such that together with the landing members, a hermaphroditic pair is formed, such as described in U.S. Pat. No. 5,713,111, or such as sold under the name Dual Lock™, available from 3M, St. Paul, Minn., USA.

Typically the first and second engaging members to be used in combination are different from one another. However, hermaphroditic first and second members, having the same function and typically the same form, are also envisaged herein. For example, the first and second engaging members may both comprise hooks.

Preferred engaging members comprise surface fastening elements or interlocking elements, or mixtures thereof, preferably mechanical fastening elements.

Preferred surface fastening engaging elements are selected from hooks including materials or fabrics having a hook-shaped structure (or hook fasteners), loops, including materials or fabrics which have a loop-shaped structure (or loop fasteners); adhesives, including pressure sensitive adhesives and thermo-activated adhesives; cohesives; magnets; vacuum providing elements (such as vacuum pads described in U.S. Pat. Nos. 4,623,296 and 3,701,592, interlocking engaging means (receptacles and projectiles; such as described in U.S. Pat. Nos. 5,545,159 and 4,946,527, describing for example interlocking bubbles and other shapes), or combinations thereof.

Preferred interlocking engaging elements may also be selected from buttons; slits; slots; holes; buckles; zips; snaps; clamps; elastic bands; elastically compressible surface extensions such as bubbles; or mixtures thereof. Preferred may be corrugating elements, obtainable by a corrugation process, e.g. the article comprising one set of corrugating elements and the change aid the other set of corrugating elements, which can be engaged by corrugation (e.g. as a jigsaw puzzle). Preferred interlocking engaging members are also described in WO 99/11211, such as the tab and slot engaging system described therein.

Highly preferred are loop-shaped materials and hook-shaped materials (i.e., VELCRO and the like). The hook-shaped materials may be made of any materials, including nylon, polyester, polypropylene. Suitable hook-shaped materials comprise a number of engaging elements, or hooks projecting away from a surface, such as a woven backing. These are for example available under the name Scotch-mate™, no. FJ3402; and also hooks such as KN081 1, KN2586, KJ6530, all available from 3M, St. Paul, Minn., USA; and hooks available from Aplix, Charlotte, N.C., USA, known as 960d, 960r or 960e. Preferred are also hooks similar to or those available from 3M, for example hooks PSL 8529 (as available in November 2000, under lot no. 85291411).

Preferred loops, in particular as landing members or elements, to be engaged with hook engaging elements, include woven fabrics or films, non-woven fabrics and films/composites whose surface is rough, to provide engagement with hooks.

It may be that the landing member loops are provided by the material of the article, e.g, the material used for the backsheet of a diaper (such as cloth-like material, as generally used for the backsheet of diapers.

However, in a preferred embodiment herein, a diaper is provided which has a backsheet, with a front crotch and back region, and a front and back waist band, each comprising two fastening tabs to fasten the diaper around the waist of the wearer, whereby the backsheet may be of material with loops, but also comprises additional engaging means, e.g. areas comprising engaging members, for example positioned between the fastening tabs of a waist band, or positioned on the back region or crotch region of the article.

Preferred loop-shaped materials include material with a plurality of fibers in the shape of loops. It may be made from a variety of materials, including nylon, polyester, polyproplene. Preferably, the loop-shaped materials have a number of fiber loops extending from a surface, such as a woven backing, such as those available under the name Scotchmate™, nylon woven no. SJ3401, from 3M, St. Paul, Minn., USA. A preferred loop-shaped material also includes tricot knit fabrics, having a plurality of (nylon) fiber loops extending from a surface of a backing, such as available under the name 'Guilford' no.16110, available from Guilford Mills, North Carolina Alternatively, the loop-shaped engaging elements may be non-woven materials. Also preferred loops are P1211999 loops, available from Aplix, Charlotte, N.C., USA and loops available as KJ7800, KN1939, available from 3M; and loops described in for example WO 92/20251, U.S. Pat. Nos. 5,595,567, 5,624,427, and 5,735,840. Preferred are also other open fiber structures such as non-wovens, for example materials which can engage with hook-like material.

Preferred are also adhesive or adhesive-containing engaging elements. The adhesives may preferably be pressure sensitive adhesives as commonly used on diaper fastening tabs, as for example described in U.S. Pat. No. 3,848,594 and as mentioned above.

Preferred adhesives are activatable, de-activatable and/or reversibly active adhesives, activated or de-activated or revised by change of pressure or temperature. For example preferred may be adhesives, which are non-tacky at low temperatures, but tacky above a certain activation temperature. Details on activatable and deactivatable adhesives can be found in U.S. Pat. No. 6,572,600 issued on 3 Jun. 2003 and U.S. Pat. No. 6,565,549 issued 20 May 2003.

Preferred are deactivatable and/or reversible adhesives that comprise a polymeric composition comprising a polymer that has a first order melting transition between about 5 degrees C. and about 50 degrees C. Preferably, the transition occurs over a melting range of less than about 10 degrees C., and more preferably over a range of less than about 5 degrees C. Such a range for the melting transition ensures that the transition from the tacky state to the substantially non-tacky state (and/or vice versa) will be quite rapid. The melting transition preferably occurs in the range of about 20 deg. C. to about 40 deg. C., and most preferably in the range of about 25 deg. C to about 37 deg. C. In alternative embodiments (e.g., thermally reversible adhesive embodiments), the polymeric composition has a freezing point lower than the deactivation temperature (e.g., skin temperature). The freezing temperature may be, for example, in the range of about 15 deg. C. to about 30 deg. C. The rate of freezing, and the associated loss of adhesion, may be increased via the addition of seeding agents as known in the art. The deactivatable and/or reversible adhesive may be a crystallizable polymer or a functional equivalent of a crystallizable polymer having a weight average molecular weight in the range of about 20,000 to 2,300,000 Daltons, typically 100,000 to 1,300,000 Daltons, more typically 250,000 to 1,000,000 Daltons. Crystallizable polymers which may be used in the adhesive include both side-chain crystallizable and main-chain crystallizable polymers, the difference being that the former class of compounds contain crystallizable side-chain moieties, and the latter class are rendered crystallizable by their backbone structure. The polymer chains in the crystallizable polymer composition may optionally be cross-linked to provide greater physical stability of the adhesive. The adhesive may optionally include additives as known in the art, such as filers, tackifiers, antioxidants, and the like. One exemplary deactivatable adhesive is described as Example 1 in U.S. Pat. No. 5,387,450. An exemplary reversible adhesive is described as Example 2 in the above-referenced U.S. Pat. No. 5,387,450. Some other examples of deactivatable and reversible adhesives suitable for use in the present invention are described in more detail in U.S. Pat. Nos. 5,156,911 and 5,648,167; which are hereby incorporated by reference herein.

In yet other embodiments, the deactivatable adhesive may be deactivated via the application of tension. For example, the adhesive, or portions thereof, may crystallize when strained, resulting in a significant or total loss of adhesive strength. Suitable tension-deactivatable adhesives are available as Poster Strips with COMMAND™ Adhesive from the 3M Corp. of St. Paul, Minn., USA, and as TESA® Power Strips from the Beiersdorf Corp. of Hamburg, Germany.

Additional suitable tension-deactivatable adhesives are described in U.S. Pat. Nos. 5,491,012; 5,626,931; 5,626,932, hereby incorporated by reference herein. Preferred cohesive are for example available from Findley under the numbers H9078 and 9054.

Preferred may be that the engaging element is one of the interlocking elements of an engaging system having slits, which interlock with other slits; button which interlock with slots or holes; hooks which interlock with holes or slots; zips which interlock with other zips; most preferably tab and slot engaging systems. Preferred interlocking elements are described in for example WO 99/11211.

Preferred may be that the change aid comprises the more expensive, more extending (e.g. if the surface comprising the engaging means is in horizontal position and the engaging means are faced upwards, the engaging means reach higher than the rest of the surface), less comfortable to wear, or more difficult to apply or process engaging element, of the engaging system, so that the article can comprise the cheaper, less extending, more comfortable to wear or easier to apply or process engaging element.

Preferred may for example be that the external change aid comprises hook engaging means, which extend from the surface of the change aid, and the article comprises loop fastening means, or that the change aid comprises button engaging elements and the article comprises corresponding holes or slots.

Preferred may be that the engaging means and/or landing member can be activated so that it is only engageable when the user activates it. For example, it may be preferred that the engaging means or landing member is covered by a closure member, such as a slide or flap, which can be opened prior to use of the engaging means (to activate the engaging means or landing member), and closed after use. Preferred may be that the closure member is sealable by engaging with the engaging members of the engaging means or landing member which it closes off. Typically, this is then such that opening of the closure member takes place with a shear or peel force which is less than the shear or peel force of the engaging system herein. Alternatively, the closure member may be sealed by fastening methods, other than the method employed by the engagement system herein; for example the flap may be sealable by an adhesive, while the engaging means comprises as engaging elements hook-shaped elements.

Also preferred may be that the engaging means or landing member is submergible from the surface of the (respectively) change and or article, upon activation, for example by application of pressure.

It may also be preferred that the engaging means or landing member, or the engaging members thereof, or part thereof, can be removed after use, to avoid subsequent unwanted engagement of the engaging means, members or elements to other items, for example the wearer's cloths or skin. For example, the landing member of the article may be removed (e.g. peeled off) after the article is applied to the wearer and the landing member is thus no longer needed for the initial application of the article, or the engaging means may be removed (e.g. peeled off) from the change aid, after use.

Preferred may also be that the engaging means (or landing member) are replaceable, so that after frequent use of the change aid, when the engaging means may become less effective, the engaging means can be replaced with a new engaging means, capable of providing effective engagement to the articles again.

The engaging means and the landing member may be a single component of the (respectively) change aid and article. Then the engaging means consist of one first engaging member, or in other words, the engaging means is equivalent to the first engaging member; and the landing member consist of one second engaging member, or in other words, the landing member is equivalent to the second engaging member. A preferred execution thereof is a change aid or article with a single engaging means or landing member in the form of a single strip, circle, dot, triangle or rectangle of engaging elements.

Preferred engaging means are such that they only engage, with the forces described herein with the landing member of the article, but not with other items, e.g. clothing of the wearer. Preferred is of course that the engaging means and landing members cannot hurt the skin of the wearer during normal use.

Preferred embodiments of the engaging members may vary, depending on the force-resistance required, size and shape of the articles to be engaged etc.

Typically, the engaging means and preferably also the landing members, are present such that the engagement which is obtained results in an article which can be held stretched or flattened at a length which is at least 80% of its maximum length, or which is such that at least part of the article can be held in a fixed position, whilst applying a force (as described above) onto a non-engaged part of the article.

More preferred may be that the engaging means, and/or the landing member is not a single component, but comprises a plurality of (respectively first and second) engaging members, which do not form a unity, e.g. which are separated from one another by areas of the aid or article, not comprising engaging elements. The engaging means or landing member may for example be a plurality of engaging members, which are be present on different surfaces, e.g. different sides, parts or components of the (respectively) change aid and article.

It may also be highly preferred that one planar surface or part or component of the change aid or article comprises a plurality of engaging members. For example, the change aid may have a (flat) planar side with a planar surface, which comprises a plurality of engaging members in the form of a plurality of dots, rectangles, stripes or mixtures thereof, with areas in between which do not comprise engaging elements. Equally, the article may take such a form. Highly preferred embodiments of the change aid, articles and combinations thereof are described herein below.

The engaging means and member and also the landing member may have any size or shape provided that the required shear forces and preferably peel forces are obtained. Typically, the engaging means has a total surface are of at least 5 cm$^2$, or even.

The engaging means can be in the form of a plurality of engaging members in the form of rectangles, having for example a surface area of (0.3 to 5)×(0.3 to 5) cm$^2$, or in the form of stripes, having a surface area of (0.3 to 5)×(6 to 40) cm$^2$.

Preferred External Change Aids

The change aid herein may be of any shape or form, which is suitable to apply the article to or remove the article from a wearer. The exact size and form will for example depend on the size and form of the article.

In a preferred embodiment the change aid is a device on which the wearer can be placed, for example whereon the wearer can lay, sit or lean. Preferred change aids are in the form of a chair, or even more preferred in the form of stiff, planar devices, e.g. rectangular devices, or for example, change mats, known in the art.

In another preferred embodiment, the change aid is a device, which is to be placed on another change device, like a change chair or preferably a change mat, preferably even to be fastened to the change mat by fastening of the fastening means to the change device.

Preferred change aids herein are stiff, as described above.

Selecting the material used for the aid, for example non-foldable, non-bendable, hard materials, such as hardened plastic, cardboard, or making the article thicker, can provide this stiffness.

The change aid may comprise restraining means, to restrict the movement of the aid, or part thereof, relative to an external object (other than the article or the wearer), or to restrict the relative movement of the aid, i.e. the movement of one part of the aid, relative to another part of the aid, for example the movement of one edge of the article, relative to another edge. Typically the restraining means is such that it holds the change aid in the same plane or under the same angle throughout use (for a single application or removal of an article). The restraining means may comprise a plurality of restraining members or elements. For example, the restraining means may be a surface modification, providing grip or gripping elements, which provide grip to an external object during use of the change aid, pincers, which attach at a specific point, or clamps, which secure a broader area of material. The restraining means may also be in the form of two restraining members or more with different coefficients of friction.

Preferred is that the restraining means are present on a side of the aid which is the opposite side to the side comprising the majority or all of the engaging members or means.

As described above, the restraining means may be any means suitable for restriction movements, typically being surface fasteners or interlocking fasteners, including those described above as useful engaging means or elements.

Preferred restraining means include adhesives, cohesives vacuum-providing elements, such as vacuum pads, described in U.S. Pat. Nos. 4,623,296 and 3,701,592.

In particular when the aid is not stiff, the provision of restraining means is very useful or even essential in some embodiments herein, to provide an effective application or removal of the article by use of the aid. Then the restraining means may be to restrain movement of one (integral) part of the aid relative to another (integral) part. Thus, the change aid may not be stiff prior to using, applying or activating the restraining means.

Preferred may be that the change aid can be reduced in size before or after use, for example by dismantling the aid, deflating the aid, or folding or rolling up the aid. This facilitates the packing of the aid, transport of the aid and storage of the aid, not only for the manufacturer but also for the user. For example if the aid is reusable, it is useful if it is portable, and that the user can easily store it away etc., by reducing its size. It may also be preferred that the aid is packed together with one or more absorbent article(s), optionally already being engaged to one article, so that it is then particularly useful if the aid can be reduced in size such that it can be easily packed with the article(s).

Hereto, it may be preferred that the aid is foldable. Also preferred may be that the aid is formed from a plurality of (separate) parts or components, one or more of which comprise the engaging means, which can be connected and disconnected.

In particular when the aid can be folded or rolled-up, deflated, or dismantled, the provision of restraining means is useful, to provide an aid which in use, does not fold or roll-up, or break up in different components, due to the force applied to the aid in use. It may be preferred that, when the aid comprises different components to be put together prior to use, the different components can be connected to one another (and thereby restrained from relative movement) by providing one or more of the components with interlocking means or surface fastening means, such as adhesive, cohesives, hooks, loops, interlocking slits, button and holes or slots, clamps, knobs and slots or holes. Preferred examples are exemplified in the figures herein.

Preferred change aids herein have at least two planar, substantially flat sides, one of which can be placed on an external object and one of which can be used to place the wearer on or against. Preferred may be that only one planar surface comprises a plurality of engaging members of the engaging means, preferably divided over that surface, preferably in the form of stripes, dots, squares, circles or triangles of engaging elements. Preferred patterns of the engaging members will depend on for example the size and shape for the article and the pattern o the landing member thereof.

When the change aid is used herein for the application or removal of infant diapers, the change aid may for example have at least one planar side of a length of at least 30 cm, or even 40 cm, or even 50 cm and a width of at least 15 cm, or even 25 cm or even 35 cm. Preferred may then be that the engaging means comprise a plurality engaging members, spaced apart such that each member engages with a different landing member, on different parts of the diaper. For example, if the diaper has a back waist band, connected to a backsheet, the engaging members may be spaced apart such that one engages with a landing member of the back waist band and one engages with a selected part of the backsheet, for example the middle portion thereof, comprising a landing member, as described hereinafter in more detail.

Preferred may be that the change aid has a planar side comprising two or more engaging members in the form of substantially longitudinal parallel stripes, as described hereinafter with references to the figures.

Preferred may also be that the aid has a planar side which has a top portion and a bottom portion, whereof the top portion comprises the engaging means, and the bottom portion is free of engaging means. Preferred may also be that the change aid has a central portion comprising the engaging means and surrounding edge portion which do not comprise the engaging means. Preferred may also be that the aid has a planar side with corner portions comprising the engaging means and a middle portion, comprising no engaging means.

It may be preferred that the change aid is at least partially made of biodegradable material, in particular when the change aid is for disposal after one or a couple of uses.

Preferred may also be that the change aid is at least partially made of a water-resistant material, or wettable material, so it can be easily cleaned and reused.

Preferred Absorbent Articles

Preferred absorbent articles herein include infant and adult diapers, training pants and pull-on pants, most preferably diapers. Preferred absorbent articles herein have elastic regions, such as cuffs and/or elasticized top or back sheets.

Preferred absorbent articles herein are diapers which have a topsheet, a core and a backsheet, which each have a front region, back region and crotch region, positioned therein between; a front waist band and a back waist band, whereby the front waist band and back waist band each have a first end portion and a second end portions and a middle portion located between the end portions, and whereby preferably the end portions comprise each a fastening system, to fasten the front waist band to the rear waist band or whereby preferably the end portions are connected to one another, and whereby the middle portion of the back waist band and/or the back region of the backsheet and/or the crotch region of the backsheet comprises a landing member, preferably the landing member comprising second engaging elements selected from loops, hooks, slots, slits, buttons, magnets. Most preferred are hooks, adhesive or cohesive second engaging elements. Preferred may be that the engaging elements on the article, or preferably diaper are provided with a means to ensure they are only engageable at certain moments, for example, they may be covered by a removable tab, which is removed when the engaging elements are to be engaged and may be re-closed when engagement is no longer needed, as described above.

Highly preferred are absorbent articles which have a specific elastic force profile which is such that the shortened article portion has a stretched shortened article length $L_s$ and a contracted shortened article length $L_c$, which are such that $L_c$ is less than 0.5 $L_s$. Preferably, $L_c$ of the article is less than 0.45 $L_s$ of the article, or even less than 0.4 $L_s$, or even less than 0.35 $L_s$, or even less than 0.3 $L_s$. Hereby, $L_s$ and $L_c$ are determined as follows:

The shortened article portion is determined by removing from each transverse end of the article a transverse strip with a width (e.g. the dimension parallel to the longitudinal axis of the article) of 20% of the article's total length (in relaxed state), so that the shortened article portion is the middle 60% of the article (in relaxed state). The shortened article length is then the length of the longitudinal axis of the shortened article, e.g. about 60% of the article length.

The stretched shortened article length $L_s$ is determined as follows:

The article is placed between to clamps in a horizontal tensile tester Z10/LH 1S, as available from Zwick (Ulm, Germany). The clamps have at least the same size as the width of the article, so that the clamps at least cover the total width of the article.

The clamps are positioned such that exactly the shortened product portion is between the clamps and such that exactly (and only) the shortened product length is uncovered by the clamps. The initial clamp distance should then be 4 cm. The measurement is done in a controlled environment, whereby the temperature is kept constant on 20° C. and the humidity on 30%. The article is then pulled in horizontal, longitudinal direction up to the moment that a force of 20 N is applied. Then, the distance between the clamps and thus between the transverse ends of the shortened article portion is measured. This is the stretched shortened article length $L_s$.

The contracted shortened article length $L_c$ is determined as follows:

After the measurement of $L_s$ above is done, the article is rested for an hour, in the controlled conditions set out above. Then, whilst still under the controlled conditions, the article is placed in the top clamp of a vertical tensile tester (as available from Zwick). On the other end a clamp with a weight of 10 grams is placed, but still supported so that the weight does not start pulling yet due to gravity.

The clamps are positioned such that exactly the shortened product length is not covered by the clamps and thus that the end of the clamps are positioned exactly at the ends of the shortened article portion. The clamps have at least the size of the width of the article at the clamping point, so that the clamps cover the total width of the article.

Then, the support for the weight is removed and the weight is hung down for 5 minutes. Then, the distance between the clamps and thus the distance between the ends of the shortened article portion is measured. This is the contracted shortened article length $L_c$.

In another preferred embodiment of the invention, the article has a topsheet, which has a specific elastic profile, and thereto, it typically comprises one or more of the elasticized regions specified herein, having an about similar elastic profile. The topsheet than has a shortened topsheet portion with a length Lt and a contracted or relaxed shortened topsheet length $Lt_c$ and a stretched shortened topsheet length $Lt_s$, determined in the manner set out above for the article.

The topsheet of the article has preferably an elastic profile, based on a two-cycle hysteresis, measured by the method below, using a 500 mm/min clamp speed, which is as follows:

1.5 Lt by a first load force of less than 1.1 N, 3.0 Lt by a first load force of less than 2.1 N and 4.5 Lt by a first load force of less than 3.0 N and a second unload force at 4.5 Lt of more than 0.9 N, a second unload force at 3.0 Lt of more than 0.5 N and a second unload force at 1.5 Lt of more than 0.1 N (provided these multitudes of Lt are below 0.8 $Lt_s$, otherwise the respective force number may not be relevant, as said out below as well).

More preferably, the profile of the topsheet is:

1.5 Lt by a first load force of less than 0.6 N, 3.0 Lt by a first load force of less than 1.1 N and 4.5 Lt by a first load force of less than 1.5 N and a second unload force at 4.5 Lt of more than 0.9 N, a second unload force at 3.0 Lt of more than 0.5 N and a second unload force at 1.5 Lt of more than 0.1 N (provided these multitudes of Lt are below 0.8 $Lt_s$, otherwise the respective force number may not be relevant, as said out below as well).

The above elastic profile of the shortened topsheet is measured by the following method, measuring the two-cycle hysteresis of said shortened topsheet portion (following ASTM 76-96):

The topsheet of an article is placed between to clamps in a horizontal tensile tester Z10/LH 1S, as available from Zwick (Ulm, Germany). The clamps are positioned such that exactly the shortened topsheet portion is between the clamps and such that exactly and only the shortened topsheet length is uncovered by the clamps (i.e. the shortened topsheet portion being that part of the topsheet that belongs to the shortened article (portion), as set out above). The clamps have at least the same size as the width of the topsheet in the clamps, so that the clamps at least cover the total width of the topsheet in the clamps. The initial clamp distance should then be 4 cm. The measurement is done in a controlled environment, whereby the temperature is kept constant on 23° C. (+/−2° C.) and the humidity on 50% (+/−2%).

The two-cycle hysteresis test is then performed, stretching the shortened topsheet (portion) up to 4.5 Lt, or 0.8 $Lt_s$, whichever is the lowest value, measuring the forces applied on the shortened topsheet during the stretching at the various stretching stages/lengths; when 4.5 Lt or 0.8 $Lt_s$ is reached, the shortened topsheet is kept in that position for 60 seconds, before the controlled relaxation back to the original position of the clamps, i.e. 4 cm distance (and the unload forces may be measured at the various stages/lengths); when the original position of clamps is reached, i.e. 4 cm distance, the shortened topsheet is held in this position for 60 seconds, before the second cycle starts, stretching the shortened topsheet up to 4.5 Lt or 0.8 $Lt_s$, optionally measuring the load forces applied at the various stages/lengths; when 4.5 Lt or 0.8 Lt$_s$ is reached again, the shortened topsheet is held in this position for 60 seconds, before the relaxation back to the original position, and the unload forces of this second unload cycle are measured for the various stages/lengths, as set out in the table above.

In this embodiment of the invention, the value of the first load and second unload forces are believed to b essential to the performance of the topsheet and representative for its elastic profile. Measurement of the first unload force and second load force may be performed, but is believed to be less representative for the force profile of the topsheet.

The topsheet preferably comprises elastic regions with elastic material which have an about similar elastic profile.

Preferred elastic materials used hereto include materials having a profile like VFE-CD, available from Tredegar®, Richmond, Va., USA, and L-86, available from Fulflex International (Limerick, Ireland), or preferably L-89, available from Fulflex, or most preferred are of course one or more of these materials itself.

The materials typically have a thickness (e.g. gauge) of at least 20 microns, more preferably at least 40 microns, or even at least 80 microns, typically up to about 300 microns, or even up to 200 microns or even up to 150 microns. Highly preferred materials have a thickness of about 100 microns.

The length and width of the elastic regions on the topsheet will vary, typically depending on the exact dimensions of the topsheet and/or the article. An elastic region may be formed from a multitude of thin strands of the elastic material, or of a single band of elastic material.

For example, for size 4 diapers, the elastic region, in relaxed state, may be about 5 to 40 mm wide, preferably 8 to 30 mm, or even 10 or even 8 to 25 mm.

In another embodiment of the invention, the article has a specific elastic profile, and thereto, it typically comprises one or more of the topsheets above and/or elasticated regions specified herein, having an about similar or the same elastic profile.

The article preferably has an elastic profile, based on a two-cycle hysteresis, measured by the method below, using a 500 mm/min clamp speed, which is as follows:

0.25 L$_s$ by a first load force of less than 0.6 N, 0.55 L$_s$ by a first load force of less than 5 N or even less than 3.5 N and 0.8 L$_s$ by a first load force of less than 10.0 N or even less than 7.0 N and a second unload force at 0.55 L$_s$ of more than 0.4 N, and a second unload force at 0.80 L$_s$ of more than 1.4 N or even more than 2.0 N.

More preferably, the profile of the article is:

0.25 L$_s$ by a first load force of less than 0.6 N, 0.40 L$_s$ by a first load force of less than 1.5 N, 0.60 L$_s$ by a first load force of less than 2.8 N, and 0.80 L$_s$ by a first load force of less than 5.4 N and a second unload force at 0.40 L$_s$ of more than 0.1 N, a second unload force at 0.60 L$_s$ of more than 0.6 N and a second unload force at 0.80 L$_s$ of more than 2.0 N.

Even more preferred is that the article has a profile of:

0.25 L$_s$ by a first load force of less than 0.3 N, 0.40 L$_s$ by a first load force of less than 0.7 N, 0.60 L$_s$ by a first load force of less than 21.4 N, and 0.80 L$_s$ by a first load force of less than 53.2 N and a second unload force at 0.40 L$_s$ of more than 0.3 N, a second unload force at 0.60 L$_s$ of more than 0.7 N and a second unload force at 0.80 L$_s$ of more than 2.0 N.

In addition, it may be preferred that the elastic profile of the article is as set out above, but then measured as a two-cycle hysteresis performed with a clamp speed of 10 mm/min.

Method of Use

The external change aid herein is used to apply or remove an article to or from a wearer. As said above, the change aid does not serve to keep the article in place, once applied, and thus, typically, the change aid and article do not stay engaged after the application is finished (if the article is removed and is disposed off, the article and change aid may remain engaged, so that both are disposed off at the same time).

Hereto, the change aid is typically engaged with the article, prior to the start of the application or removal of the article. The article and change aid may be packed together in already engaged position, so that when the user opens the pack, the engaged article and change aid are ready for use. More preferred is that the article is separate from the change aid and is engaged to the change aid on the moment this is required, e.g. when the article needs to be applied to the wearer.

The engagement of the change aid and the article can be done in any way, provided that the receiving means of the change aid and the landing member of the article are positioned such that they are engageable, e.g. well aligned. Typically, the change aid is placed on or against an external object, preferably on a flat surface of the external object, and then the article is brought into contact with the change aid, typically placed on top of the change aid, and the engaging system is engaged. Then the article is applied to the wearer and the change aid is disengaged from the article; or the article is removed from the wearer and optionally the change aid is removed from the article.

In a preferred execution, the article is an infant diaper. Then it is preferred that the change aid and article are engaged prior to, or simultaneous with or subsequent to bringing the diaper in contact with the infant, but preferably prior to bringing the article in close contact with the infant. Thus preferably, the diaper is engaged with the change aid and then the infant is paced against, or preferably on top of the engaged article. Then the article can be pulled around the wearer's body, e.g. from the back of the infant, between its legs, to the front of the infant, with much more ease, because the diaper is held in place by the change aid. The diaper can then be fastened to the wearer, e.g. by fastening the fastening means on the diaper to one another. Then, the diaper can be disengaged from the change aid, typically by the force required to lift the infant from the change aid, or by peeling or pulling the change aid of the diaper.

In another preferred embodiment, the article is an adult diaper. The change aid can then be used to aid to adult wearer to apply or remove the diaper form itself, or to aid a care-taker to apply or remove the diaper from the adult wearer.

The change aid may then be disposed of, or in a preferred embodiment the change aid is reusable (and preferably washable) and can be used for a following change.

A preferred method for applying the article by use of the change aid comprises thus the steps of a) obtaining an article engaged to an external change aid as described herein, (preferably by first engaging the second engaging elements of the landing member of the article and the first engaging elements of the engaging means of the external change aid);

b) placing the engaged article-change aid of a) in close proximity to the wearer's body;

c) fastening said article around or to the wearer's body;

d) disengaging the first engaging element and the (second engaging elements of the article, to disengage the article and the change aid.

In one embodiment, the article can be flattened or stretched out to about the complete product length, typically at least 70% or even at least 80% of the full product length, as defined herein, by ensuring that at least the opposite ends (in direction of length) are engaged, as discussed below referring to the figures. It may also be preferred to only engage one end, so that only part of the article is flattened or stretched, as can be seen in the figures herein.

In a preferred embodiment the article has an elastic component(s) and application of the article requires stretching the article and thereby extending the elastic component (s), thus applying a force on the article to counter act the elastic forces of the article. Preferred for example is that the article has elastic leg cuffs or more preferably an elasticized topsheet, as described above, and that the article has to be stretched around the wearer's body. If the change aid were not be engaged to the article, it is very likely that the article is not stretched properly around the wearer's body, or is released prior to fastening it to the wearer's body and springs back to the original, unstretched position. By use of the change aid, the elastic article can be stretched while a part of the article is held in place by the change aid. The article can thus be more easily and accurately stretched and fastened around the wearer's body.

If the change aid comprises restraining means, this is used or activated prior to, simultaneously with or after engaging the article to the change aid. For example, the restraining means may be surface fastening means, which are engaged to a surface of an external object, prior to engaging the article to (the opposite side of) the change aid. For example, the restraining means may restrain two part or more of the change aid from moving relatively to one another (e.g. by fastening two separate or integral parts such that no or little relative movement is possible and the change aid is thus stiff) and the article is attached to one part of the change aid, prior to restraining/fastening the two or more parts of the change aid; or the article is attached to one or more of the parts of the change aid after the restraining/fastening means is applied, as is described in more detail below, with reference to the figures.

DETAILED DESCRIPTION OF THE FIGURES

In FIG. 1a, a change aid in the form of a change mat (100) is shown, which has an engaging means comprising 4 engaging members (120, 121, 122, 123) in the form of rectangular areas comprising hook-shaped engaging elements, for example VELCRO hooks. The change mat (100) comprises a washable cover, for example a plastic cover, whereto the engaging members (120, 121, 122, 123) are attached. The mat comprises a soft material, positioned under the top cover and on top of a rigid material. The rectangular areas of engaging members (120, 121, 122, 123; herein 'rectangles') are positioned such that both small size diapers (130) and large size diapers (130) can be engaged to the mat (100). In FIG. 1a it is shown that the rectangles (120, 121, 122, 123) are thereto positioned on at least the bottom 45–25 cm of the length of the mat, typically about 35 cm, and on the middle 15–25 cm, typically about 20 cm, of the mat (100). The rectangles (120, 121, 122, 123) are preferably positioned in a rectangular or rectangular pattern, as can be seen in FIG. 1a. The rectangles (120, 121, 122, 123) have preferably surface area of (1 to 5 cm)×(1 to 5 cm), preferably about (2 to 2.5 cm)×(2 to 2.5 cm).

Figure 1B:
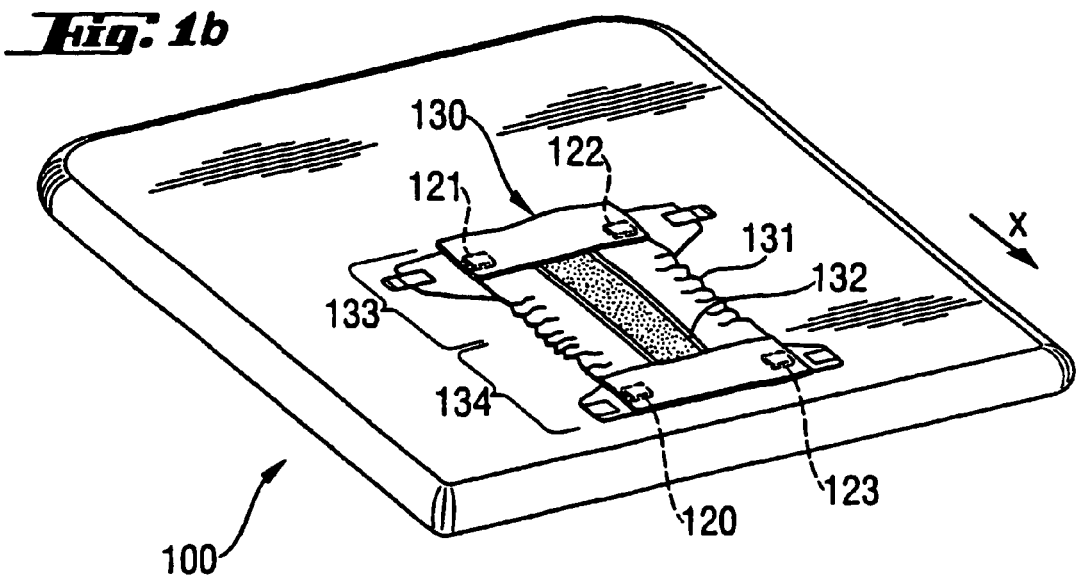
Figure 1C:
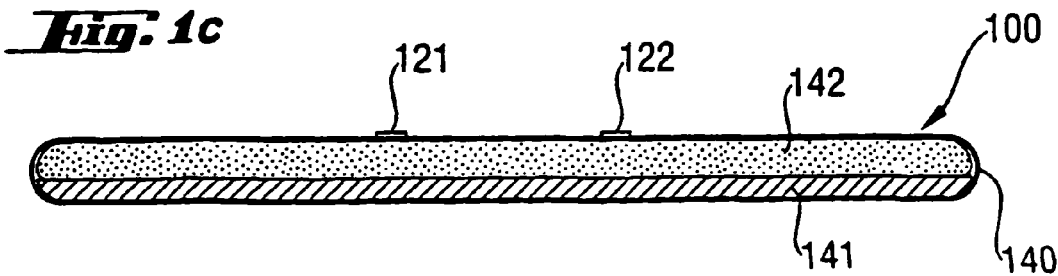
FIG. 1c shows the change mat of FIG. 1a with an elasticized diaper, engaged to the four engaging members, held in a stretched position.

In FIG. 1b, it is shown how a diaper (130) which has elastic leg cuffs (131) and an elasticized region (132) on the topsheet, of the type described above in more detail, is engaged to all 4 engaging members/rectangles (120, 121, 122, 123), and held in this stretched position. This is achieved by for example first engaging the top two rectangles (121, 122) to the back region (133) of the backsheet of the diaper (130), which comprises fibrous material in the form of loops on its entire backsheet surface. Then, the front region (134) of the diaper (130) is pulled in x-direction, and is thereby stretched. Then, the front region (134) of the backsheet of the diaper (130) is engaged with the bottom two engaging members/rectangles (120 and 123). The baby can then be placed on top of the diaper (130) of FIG. 1c, where after the front region (134) of the diaper (130) can be disengaged from the two bottom rectangles (120, 123). Then, the 4 waistband tapes of the diaper (130) can be fastened to one another, to fasten the diaper (130) to the baby. Then, the top two engaging members/squares (121, 122) can be disengaged from the diaper (130) and the baby can be lifted with the diaper (130) on, from the change mat (100).

Figure 2A:
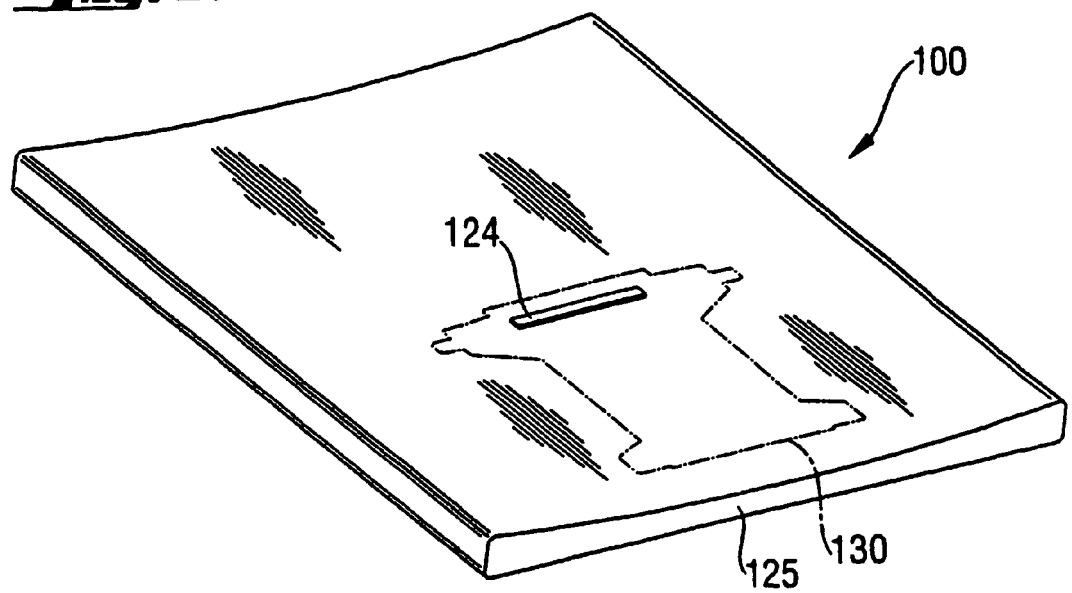
FIG. 2a shows a top view of a rigid change mat of the invention having one rectangular engaging member.

In FIG. 2a, a change aid in the form of a planar, substantially flat change mat (100), similar to the mat shown in FIG. 1a) is shown, with the difference being that the change mat (100) has only one stripe (124; being the engaging means) with engaging elements.

The stripe (124) is preferably between 5 and 30 cm long and 0.5 to 3 cm wide, more preferably between 15 and 25 cm long and 1 to 2.5 cm wide.

The strip (124) comprises preferably VELCRO hooks and/or adhesives as engaging elements.

Figure 2B:
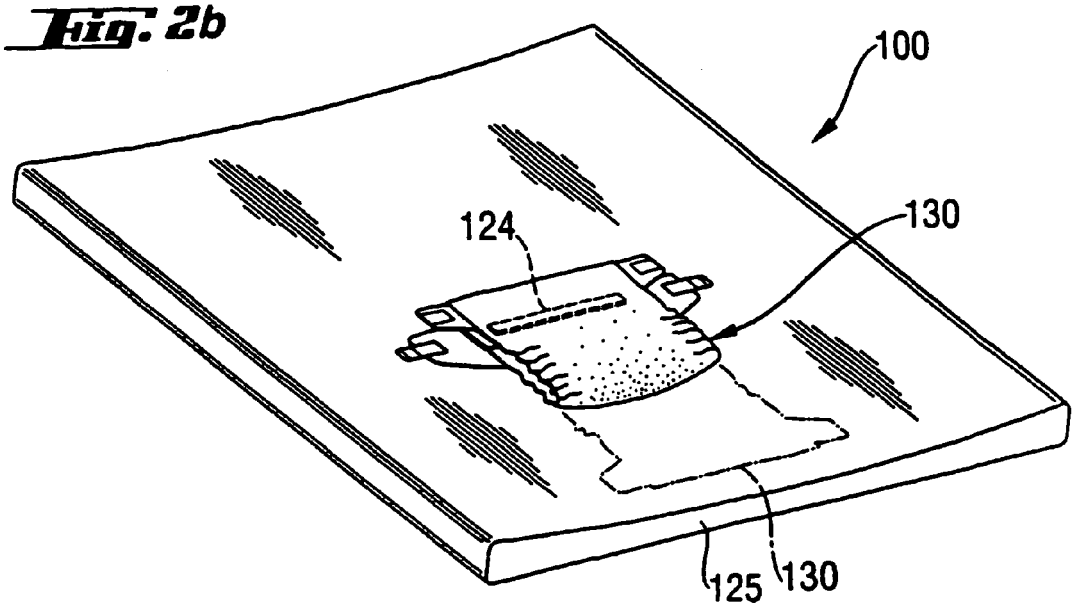
FIG. 2b shows a perspective view of a change mat having one engaging member, to which an elasticized diaper is engaged and held in position.

FIG. 2b shows how the diaper in folded position can be engaged to part of the change mat (100).

The strip (124) is preferably positioned on the change mat (100) such that the diaper engaged to the strip (124) on the mat (100) can be stretched or flattened out to beyond the end (125) of the change mat. Namely, it may be preferred that, when applying the diaper on a baby, the diaper is connected to the change mat (100), as described above and then stretched out beyond the end (125) of the change mat (100), so that the extending portion of the diaper can be easily positioned between the change mat (100) and the body of the person applying the article, so that the diaper does not 'spring' back to the original position.

Figure 3A:
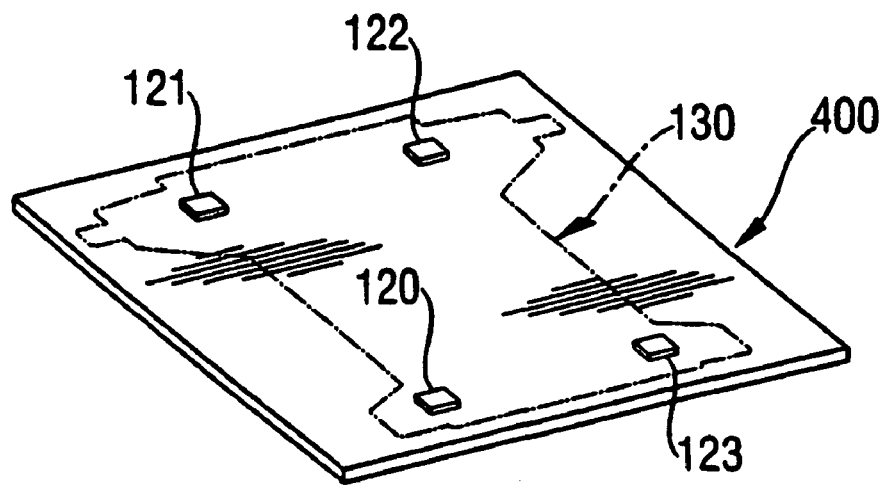
FIG. 3a shows a top view of a change aid of the invention, in the form of a piece of rigid cardboard, having four rectangular engaging members.
Figure 3B:
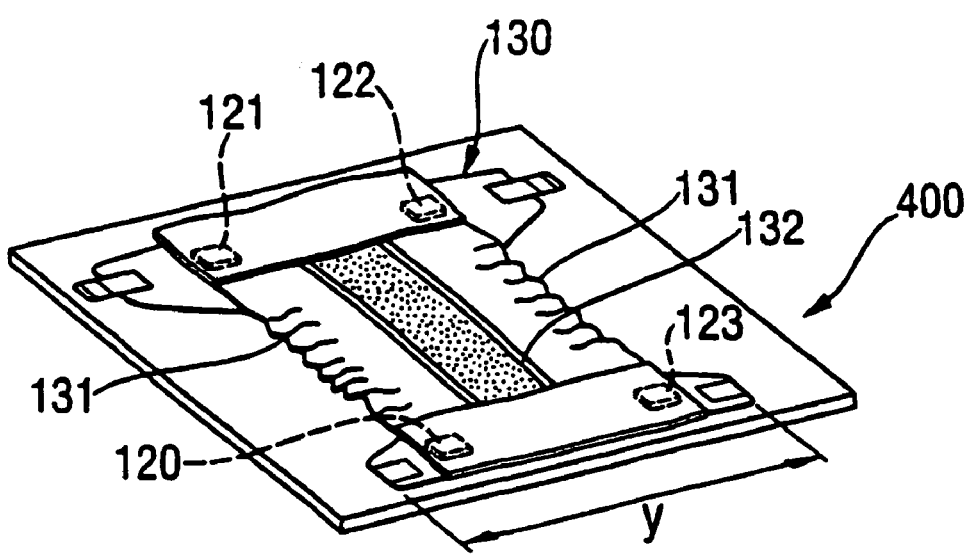
FIG. 3b shows the change aid of FIG. 3a with an elasticized diaper, engaged to the four engaging members, held in a stretched position.

In FIG. 3a, a change aid in the form of a rectangular, rigid cardboard device (400) is shown. It is a little wider than the width of an avenge diaper (130; the width being train the distance from one end of a fastening tape to the other end of a fastening tape of the diaper, being the distance or length y in FIG. 3b), and a little longer than the length of an average diaper (130). The cardboard device comprises 4 rectangular engaging members (120, 121, 122, 123), as in FIGS. 1a and 1b, except that the length from rectangle 120 to 122 is preferably about 45 cm. The diaper (130) is engaged and disengaged as described above under FIGS. 1a and 1b, and as can be seen in FIG. 3b.

The cardboard device (400) is typically placed on a change mat prior to or after engagement of the diaper (130), in a way normally done with diapers.

The device (400) may comprise restraining means on the opposite side (or back of the device), opposite to the side with the engaging members (120, 121, 122, 123), to restrain the device (400) from relative movement to the surface on which it is placed, e.g. a change mat. For example, the back of the device (400) may comprise areas of VELCRO hooks or areas with adhesive, which can be fastened to a change mat, which is such that it adheres to the adhesive or VELCRO hooks.

Of course, the device as shown in FIGS. 3a and b may be made of different materials, including plastic, rubber, woven and non-woven fabrics, provided it is stiff or can be made stiff by application of restraining means on the device. Of course, it may also have different sizes or patterns of engaging means and different types of engaging means, depending on the landing zones on the diaper, for example.

Figure 4A:
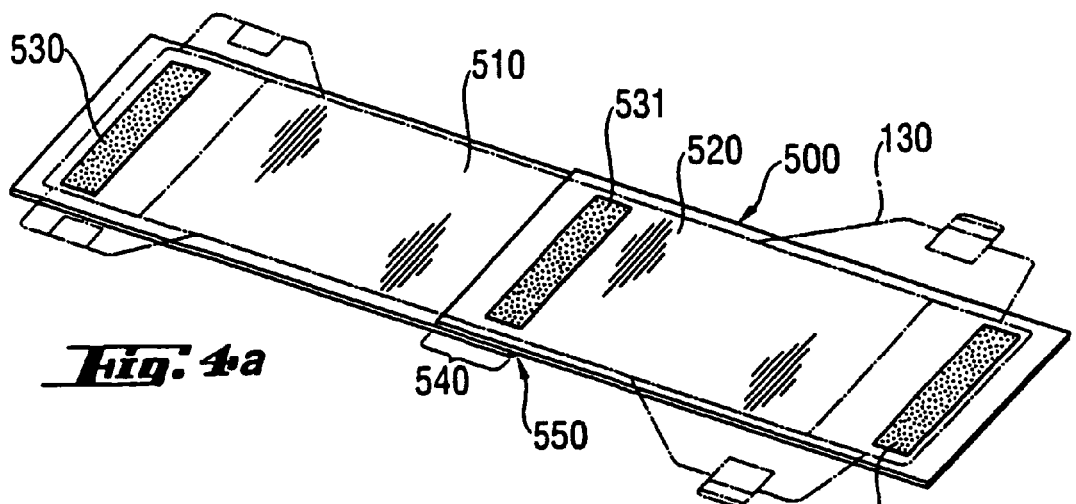
FIG. 4a shows a schematic top view of a foldable change aid made of two parts, which are fastened such that the change aid becomes rigid. The change aid has in total three engaging members.

FIG. 4a shows a change aid (500) in the form of change device (500) which has two separate cardboard parts (510 and 520): a first part (510), comprising preferably one engaging member in the form of a strip (530), with engaging elements, and a second part (520), comprising typically two engaging members (531 and 532) in the form of strips, with engaging elements.

The two parts (510, 520) can be restrained from relative movement, to provide a stiff change device (500), similar to the device shown in FIG. 3b.

Figure 4B:
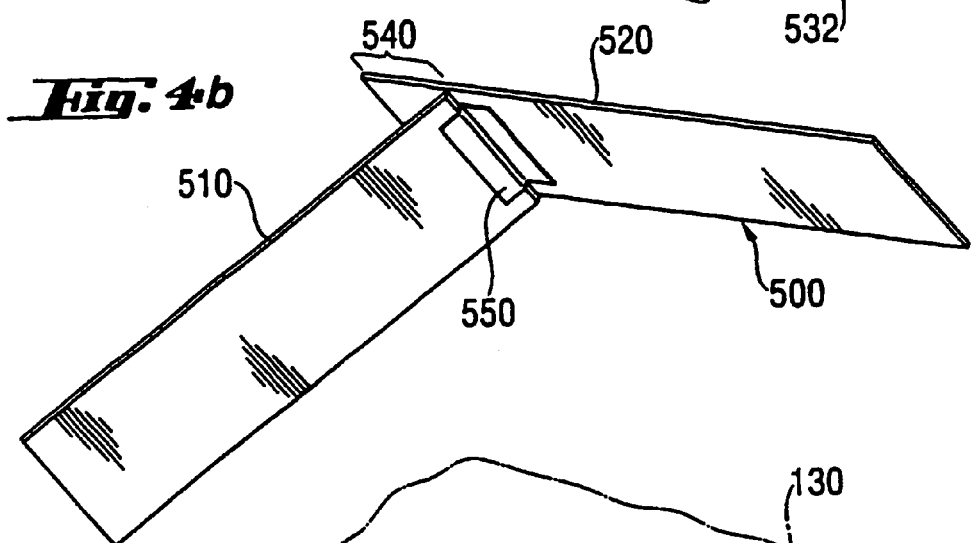
FIG. 4b shows a perspective view of the change aid of FIG. 4a, while it is not yet completely unfolded.

For example, as shown in FIG. 4b, the two parts (510, 520) may be connected by only a hinging area (550), i.e. the area on one side of one of the parts (520) which connects with an edge of the other part (510), and may be rotated around the axis of this hinging area (550) so that the two parts (510, 520) are rotated to be in one plane, and have the final length of the device (500). The two parts (510, 520) may be positioned on top of one another (not shown), prior to use; then, the device is for example about half of its final length in use. The parts (510, 520) are then rotated around the axis of the hinging area (550), to reach the above mentioned position, whereby the two parts (520, 530) are in one plane, having the final (full) length of the device (500). The two parts (510, 520) of the device (500) may then be such that there is a zone of overlap (540) between the two parts (510, 520), which ensures that the parts (510, 520) can not rotate any farther than to this position, as can be seen in FIG. 4a. Of course, the two parts (510, 520) can be rotated backwards, into their original position whereby the parts (510, 520) are about fully overlapping, the device (520) then thus having about half the full (final) length.

The engaging means is positioned on the sides, which are opposite to the side where the hinging area (550) is, i.e. opposite to the side where the edge of one part (510) connects to the (opposite) surface of the other part (520). This ensures that when the diaper (130) is engaged to the two parts (510, 520) of the device (500) and subsequently has to be removed from the two parts (510, 520) of the device (500), the device (500) can move in the direction of the pulling forces, i.e. this ensures that the device (500) is stiff.

The parts (510, 520) of the device (500) may comprise for example 3 engaging members in the form of strips (530, 531, 532) forming together the engaging means, and comprising engaging elements, such as for example adhesive and/or VELCRO hooks. However any other type, shape or design of engaging means can be used on this changing device (500).

The strips (530, 531, 532) may be any size, as also mentioned above, for example between 5 and 30 cm long and 0.5 to 3 cm wide, more preferably between 10 and 20 cm long and 1 to 2.5 cm wide. The strips 530 and 531 and the strips 531 and 532 may be spaced apart by for example 5 to 30 cm, preferably about 10 to 25 cm, typically such that the strips 530 and 532 are spaced apart with about 20 to 60 cm, preferably 30 to 45 cm.

Figure 4C:
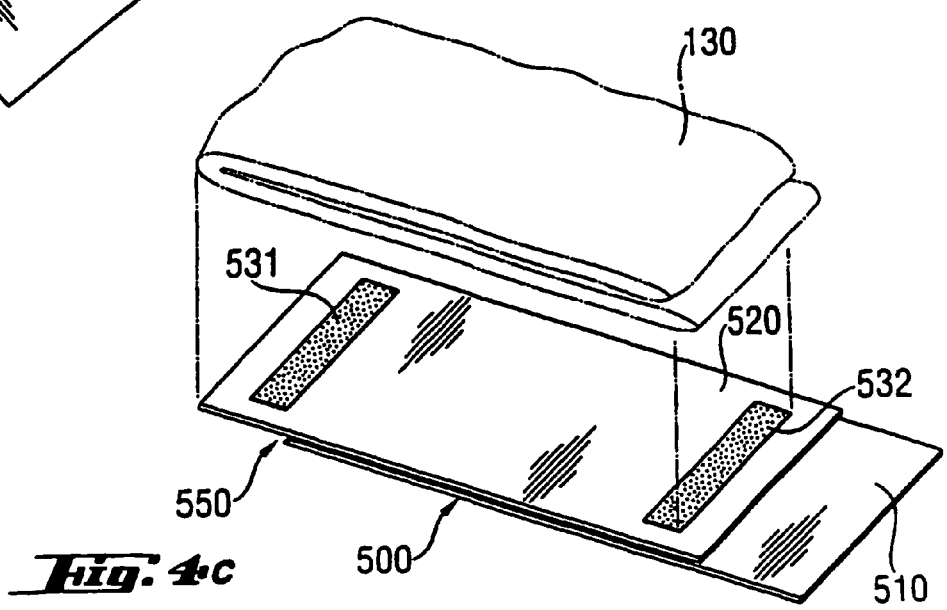
FIG. 4c shows the change aid of FIGS. 4a, 4b and 4c, having an elasticized diaper partially engaged to said change aid.

As is shown in FIG. 4c, the change device (500) can be pre-engaged to the diaper (130), by pre-engaging for example one part (520) of the device (500) to part of the diaper, e.g. by engaging strips 532 and 531 to part of the backsheet of the diaper (130). The diaper (130) and change device (500) may be packed for sale in a pre-engaged position.

Then, the parts (510, 520) of the change device (500) are rotated as described above, to the planar, full length position/ then the diaper (130) can be flattened or stretched and engaged with the remaining strip 530. Then the change aid (500) and the diaper (130) are in stretched or flat position, and the baby can be packed on top of the diaper (130). Then, the diaper (130) can be partially disengaged horn the change device (500), typically by disengaging strip 530, and the diaper (130) can be attached to the baby, for example by fastening the fastening tapes of the diaper (130) around the waist of the baby. Then the remaining part of the diaper (130) can be disengaged from the change device (500), typically by disengaging the strips 531 and 532. The change device (500) can then be rotated back into its original position (e.g. where by the two part (510, 520) are on top of each other, overlapping each other) and it can be re-used or dispensed of.

Of course the change aid (500) as shown in FIGS. 4a, b and c can be modified to use different means to restrain the relative movement of the two parts (510, 520) relative to one another. For example, the two parts (510, 520) may slide over one another, so that, by pulling one or both parts (510, 520) in out ward direction (opposite direction if both are pulled out wards), to obtain an elongated change aid (500), e.g. of about the length equaling the combined length of the two parts (510, 520). To ensure that the parts (510, 520) do not move when a force perpendicular on the force required to slide the parts, is applied, the parts (510, 520) are attached to one another by restraining means along the longitudinal edges, for example by clamps. Thus, when a diaper (130) is engaged to the change aid (500) which is in horizontal flat position, and subsequently is removed by a upwards pulling force, then the two parts (510, 520) are restrained from moving in the direction of the pulling force, e.g. along with the diaper (130). Because the device (500) is restrained from this relative movement, the diaper (130) is easily removed after application of the diaper (130) to the baby.

The change aid (500) may be of cardboard, or plastic or any other suitable material that can be made stiff by use of the above described restraining means.

Of course the change aid (500) may also comprise more than two parts (510, 520), which each can be moved (rotated) such as to form a change aid of the full length, e.g. by two or more hinging areas (550) and overlap zones (540) three parts or more.

As mentioned above, the change aid (500) may have additional restraining means, for example positioned on the opposite side to the side comprising the engaging means. Such restraining means can then for example be fastened to an external surface such as a change mat or change table, for example by use of adhesives or VELCRO restraining means, as described above.

The change aid (500) of FIGS. 4a, b and c may also be modified such that the two parts (510, 520) are not connected in prior to use, such that they are thus two (or more) separate parts (510, 520), which are then connected prior to use. Examples of such change aids are shown in FIGS. 5a, 5b, 5c, 5d and 6a and 6b.

For example, the change aid (600) with two separate parts (601, 602) as shown in FIG. 5a) can be connected and restrained from movement by use of one or more areas (610, 611) which can engage, such as a set of interlocking areas, adhesive areas, VELCRO hooks and loops, magnets, cohesives.

For example, as shown in FIG. 5b, the change aid (600) may also be two separate parts (601, 602) which are not connected prior to use, but whereof one (or more) of the parts (602) has one or more slits (620, 621), dividing the edge of one (or more) of the parts (602) in tabs (623, 624, 625), which can slide over or under the edge of another part (601), to thus restrain the movement of the two parts (601, 602), similar to the restraining describe above.

For example, as shown in FIG. 5c, the change aid (600) may also be two separate parts (601, 602) which are not connected prior to use, but whereof one (or more) of the parts (602) has one or more clamps (630, 631), which can slide over or under another part (601), to thus restrain the movement of the two parts (601, 6020, similar to the restraining describe above.

An alternative type of clamps shown in FIG. 5d, where a change aid (600) is shown which has two (separate) parts (601, 602) which are (to be) connected prior to use, by use of one or more side clamps (640). The clamp or clamps (640) may be connected to one or more of the parts (601, 602), or the parts (601, 6020 and the clamp(s) (640) may all be separate, and to be connected prior to use, to thus restrain the movement of the two parts (601, 602), similar to the restraining describe above.

Figure 6A:
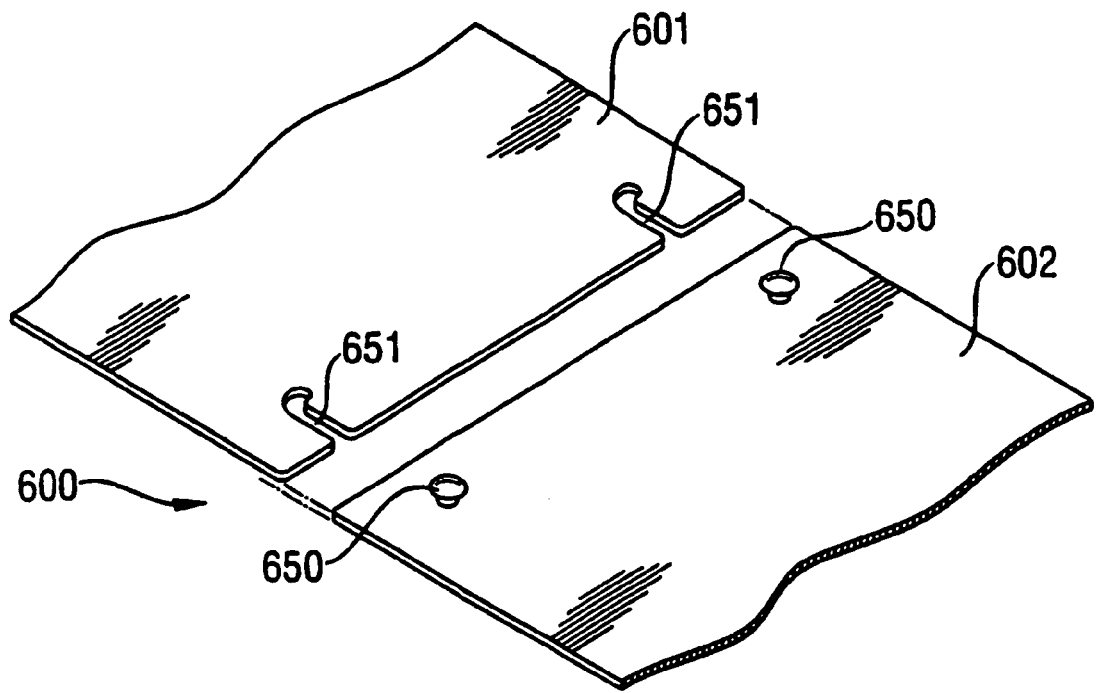
FIG. 6a shows a perspective view of a change aid with two separate parts, one of which is shown to comprise four rectangular engaging members, and having means to make the two parts stiff or rigid, i.e. restrict their movement, relative to one another.
Figure 6B:
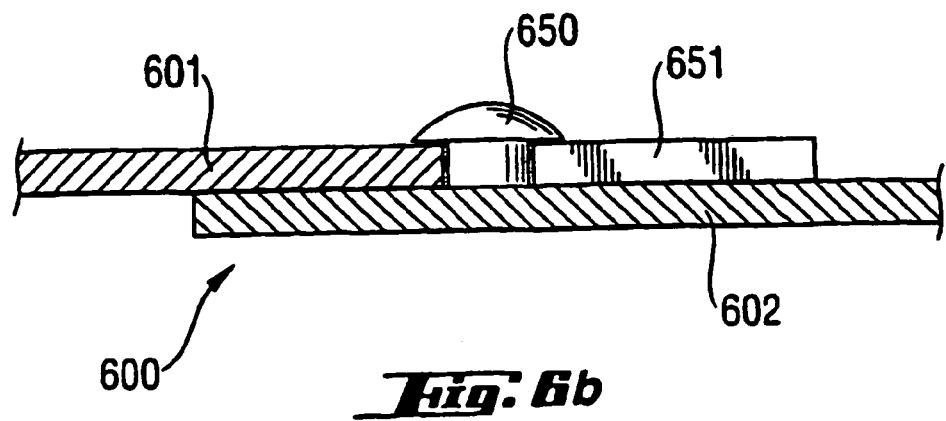

For example, as shown in FIGS. 6a and 6b, the change aid (600) may also be two separate parts (601, 602) which are not connected prior to use, but which are connectable by restraining means in the form of a slot (651) and knob (650) arrangement, whereby one part (601) of the change aid (600) comprises the slot (651) and one part (602) of the change aid (600) comprises the knob (650). The knob (650) can easily slide into the slot (651), to thus restrain the movement of the two parts (601, 602), similar to the restraining describe above.

FIGS. 7a and b show another preferred change aid, in the form of a change mat (100), which is in one part, but folded to form a multitude of layers. The change mat (100) can be unfolded before use. Typically, the change mat (100) is of a stiff material, or the change mat (1000 is such that when positioned on a flat, substantially horizontal surface, with the inside angle of the folds facing the surface, the change mat (100) becomes stiff, such that it can not move or only partially move when an upwards pulling force is applied, such as when the diaper (130) is removed from the change mat (100). The change mat (100) may be made of material as the change mat (100) described above under FIG. 1.

Of course, all the change aids as shown in the figures can equally be used to remove a diaper from the wearer.

What is claimed is:

1. An external change aid comprising a flat changing mat having a planar side having areas comprising engaging means and areas not comprising such engaging means, said engaging means being adapted to engage with and hold portions of an absorbent article adapted to be worn externally on a lower torso of a wearer and having fastening means, the engaging means being adapted to engage with and hold the portions of the absorbent article while the fastening means is used to fasten the absorbent article in place for wearing or while the fastening means is unfastened for removal of the absorbent article and thereby assist in the respective application or removal of said absorbent article when so engaged.

2. The external change aid as in claim 1, wherein the engaging means comprises one or more engaging members in the form of stripes, rectangles, dots, circles or triangles.

3. The external change aid as in claim 2, wherein the engaging members comprise engaging elements selected from interlockable elements, hooks, loops, adhesives, cohesives, or combinations thereof.

4. The external change aid as in claim 3, wherein the engaging means is adapted to releasably engage the absorbent article by an application of pressure on said engaging means.

5. The external change aid as in claim 2 wherein one or more of said engaging members has the form of a stripe having a width of between 0.5 cm and 5 cm.

6. The external change aid as in claim 1, wherein the planar side has a top portion and a bottom portion and only the bottom portion comprises said engaging means.

7. The external change aid as in claim 1 wherein the changing mat is foldable.

8. The external change aid of claim 7 wherein the foldable changing mat is stiffened by being unfolded for use.

9. The external change aid as in claim 1 having restraining means disposed on an opposing planar side and adapted to fasten the external change aid to an external object.

10. The external change aid as in claim 9 comprising at least two parts connectable by said restraining means.

11. The external change aid of claim 1 wherein the engaging means is adapted to engage with a landing member on the absorbent article.

12. The external change aid of claim 11 wherein the landing member comprises loops and the engaging means comprises hooks adapted to engage with the loops of the landing member.

13. An article of commerce comprising a package containing an external change aid comprising a changing mat having a planar side having areas comprising engaging means and areas not comprising such engaging means, wherein the planar side has a top portion and a bottom portion and only the bottom portion comprises said engaging means, said engaging means comprising one or more engaging members in the form of stripes, rectangles, dots, circles or triangles, said engaging members comprising engaging elements selected from interlockable members, hooks, loops, adhesives or cohesives, and also containing an absorbent article adapted to be worn externally on a lower torso of a wearer, wherein said engaging means is adapted to engage with said absorbent article and thereby assist in the application or removal of said absorbent article when so engaged.

14. The article of commerce of claim 13, wherein the external change aid is pre-engaged wit the absorbent article.

15. The article of commerce of claim 14, wherein the package contains additional absorbent articles not engaged with the external change aid.

16. The article of commerce of claim 13, wherein the engaging elements comprise hook fasteners and the absorbent article comprises a landing member comprising loops adapted to engage with the hook fasteners.

17. The article of commerce of claim 13, wherein the absorbent article is a diaper having an elastic topsheet.

18. The article of commerce of claim 13 wherein the absorbent article comprises a landing member disposed on a back exterior surface of the absorbent article and adapted to engage wit the external change aid.

19. A method comprising the steps of:
  a) providing an absorbent article adapted to be worn about a lower torso of a wearer;
  b) providing an external change aid comprising a changing mat having a planar side having areas comprising engaging means adapted to engage with said absorbent article and thereby assist in the application or removal of said absorbent article when so engaged;

c) engaging the external change aid with the absorbent article;

d) placing the engaged absorbent article and external change aid in close proximity to the wearer's lower torso;

e) fastening the absorbent article around or to the wearer's lower torso;

f) disengaging the absorbent article from the external change aid.

20. The method of claim 19 further comprising the step of restraining the external change aid to restrict the movement of the external change aid in relation to an external object by fastening the external change aid to said external object prior to engaging the external change aid with the absorbent article.

* * * * *

UNITED STATES PATENT AND TRADEMARK OFFICE
CERTIFICATE OF CORRECTION

PATENT NO. : 6,981,289 B2  
DATED : January 3, 2006  
INVENTOR(S) : Mueller et al.

It is certified that error appears in the above-identified patent and that said Letters Patent is hereby corrected as shown below:

Column 9,  
Line 27, delete "KN08 1" and insert -- KN0811 --.  
Line 63, after "Carolina", insert -- . -- (a period).

Column 17,  
Line 8, before "essential", delete "b" and insert -- be --.

Column 20,  
Line 46, delete "avenge" and insert -- average --; delete "train" and insert -- from --.

Column 22,  
Line 10, delete "horn" and insert -- from --.

Column 24,  
Lines 48 and 61, delete "wit" and insert -- with --.

Signed and Sealed this

Twenty-first Day of March, 2006

JON W. DUDAS  
*Director of the United States Patent and Trademark Office*